(12) United States Patent
Debreczeny et al.

(10) Patent No.: US 8,989,832 B2
(45) Date of Patent: *Mar. 24, 2015

(54) PHOTOPLETHYSMOGRAPHY WITH CONTROLLED APPLICATION OF SENSOR PRESSURE

(71) Applicant: Covidien LP, Mansfield, MA (US)

(72) Inventors: Martin P. Debreczeny, Danville, CA (US); Rafael Ostrowski, Pittsbrug, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/922,849

(22) Filed: Jun. 20, 2013

(65) Prior Publication Data

US 2013/0289371 A1    Oct. 31, 2013

Related U.S. Application Data

(63) Continuation of application No. 12/543,908, filed on Aug. 19, 2009, now Pat. No. 8,494,606.

(51) Int. Cl.
*A61B 5/1455* (2006.01)
*A61B 5/00* (2006.01)

(52) U.S. Cl.
CPC ........... *A61B 5/14551* (2013.01); *A61B 5/6843* (2013.01); *A61B 5/6826* (2013.01); *A61B 5/6838* (2013.01)
USPC ........................................................ 600/335

(58) Field of Classification Search
CPC .............. A61B 5/1455; A61B 5/14551; A61B 5/14552; A61B 5/6826; A61B 5/6838; A61B 5/6843

USPC ................................. 600/310, 322, 323, 335
See application file for complete search history.

(56) References Cited

U.S. PATENT DOCUMENTS

| 4,927,264 | A | 5/1990 | Shiga et al. |
|---|---|---|---|
| 5,522,388 | A | 6/1996 | Ishikawa et al. |
| 5,817,008 | A | 10/1998 | Rafert et al. |
| 6,078,828 | A | 6/2000 | Yasuda et al. |
| 6,151,516 | A | 11/2000 | Kiani-Azarbayjany et al. |
| 6,222,189 | B1 | 4/2001 | Misner et al. |
| 6,947,781 | B2 | 9/2005 | Asada et al. |
| 7,263,395 | B2 | 8/2007 | Chan et al. |
| 7,747,301 | B2 | 6/2010 | Cheng et al. |
| 8,190,229 | B2 | 5/2012 | Lowery et al. |
| 2006/0224053 | A1 | 10/2006 | Black et al. |

FOREIGN PATENT DOCUMENTS

| JP | 2004148070 A | 5/2004 |
|---|---|---|
| JP | 2006075354 A | 3/2006 |
| JP | 2007330708 A | 12/2007 |
| WO | 2004006748 A2 | 1/2004 |

*Primary Examiner* — Eric Winakur
(74) *Attorney, Agent, or Firm* — Fletcher Yoder PC

(57) ABSTRACT

Systems, methods, and devices for obtaining consistently reproducible diagnostic measurements with a photoplethysmographic sensor are provided. In one embodiment, a method for obtaining such a diagnostic measurement includes applying a pressure between a photoplethysmographic sensor and a patient, increasing the pressure until the photoplethysmographic sensor outputs a plethysmographic waveform of minimal amplitude, decreasing the pressure by a predetermined fraction, and obtaining a diagnostic measurement using the photoplethysmographic sensor. The pressure may be applied using a pressure device that includes, for example, a clip, a wrap, an inflatable balloon or bladder, or an inflatable cuff, or any combination thereof.

20 Claims, 7 Drawing Sheets

PHOTOPLETHYSMOGRAPHY WITH CONTROLLED APPLICATION OF SENSOR PRESSURE

This application is a continuation application of U.S. patent application Ser. No. 12/543,908, entitled "Photoplethysmography with Controlled Application of Sensor Pressure", filed Aug. 19, 2009, which is herein incorporated by reference in its entirety.

BACKGROUND

The present disclosure relates generally to non-invasive diagnostic measurements dependent on pulse spectra and, more particularly, to photoplethysmographic measurements taken with a controlled application of pressure.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Diagnostic measurements, such as pulse oximetry and non-invasive measurements of total hemoglobin, may be determined from pulse spectrum measurements at varying wavelengths of light. For example, pulse oximetry may involve measurements at wavelengths of approximately 660 nm and 900 nm, and non-invasive measurements of total hemoglobin may involve measurements of wavelengths of approximately 1320 nm and 800-900 nm. In operation, conventional two-wavelength photoplethysmographic sensors may emit light from one or more emitters (e.g., light emitting diodes (LEDs) or fiber optic cables to one or more remote light sources) into a pulsatile tissue bed and collect the transmitted light with a detector (e.g., a photodiode or fiber optic cables to a remote photodetector). The detected light may then be utilized to estimate, for example, a level of oxygen saturation in the blood that is present in the tissue bed. The emitters and detector may be positioned in various orientations. In a transmission-type photoplethysmographic sensor, the emitters and detector are positioned substantially opposite one another (e.g., on opposite sides of a patient's finger), while in a reflectance-type photoplethysmographic sensor, the emitters and detector are placed adjacent to one another.

Signals from a photodetector of a photoplethysmographic sensor may be decoded to ascertain a plethysmographic waveform, which may be due to the cycling light attenuation caused by the varying amount of arterial blood that the light from the emitters passes through. Various factors may cause diminished signal quality or cause inconsistent or unreliable plethysmographic waveform readings. Specifically, the presence of excessive extravascular fluid or venous blood in a tissue bed of interest may interfere with the detection of arterial blood, producing inaccurate or inconsistent plethysmographic waveforms. The quantity of extravascular fluid or venous blood in a tissue bed of interest may vary from patient to patient or from time to time for the same patient.

SUMMARY

Certain aspects commensurate in scope with the originally disclosed embodiments are set forth below. It should be understood that these aspects are presented merely to provide the reader with a brief summary of certain forms the embodiments might take and that these aspects are not intended to limit the scope of the presently disclosed subject matter. Indeed, the embodiments may encompass a variety of aspects that may not be set forth below.

The present disclosure relates to systems, methods, and devices for obtaining consistently reproducible diagnostic measurements with a photoplethysmographic sensor. In one embodiment, a method for obtaining such a diagnostic measurement includes applying a pressure between a photoplethysmographic sensor and a patient, increasing the pressure until the photoplethysmographic sensor outputs a plethysmographic waveform of minimal amplitude, decreasing the pressure by a predetermined fraction, and obtaining the diagnostic measurement using the photoplethysmographic sensor. The pressure may be applied using a pressure device that includes, for example, a clip, a wrap, an inflatable balloon or bladder, an inflatable cuff, or any combination thereof.

BRIEF DESCRIPTION OF THE DRAWINGS

Advantages of the presently disclosed subject matter may become apparent upon reading the following detailed description and upon reference to the drawings in which.

DETAILED DESCRIPTION OF SPECIFIC EMBODIMENTS

Figure 1:
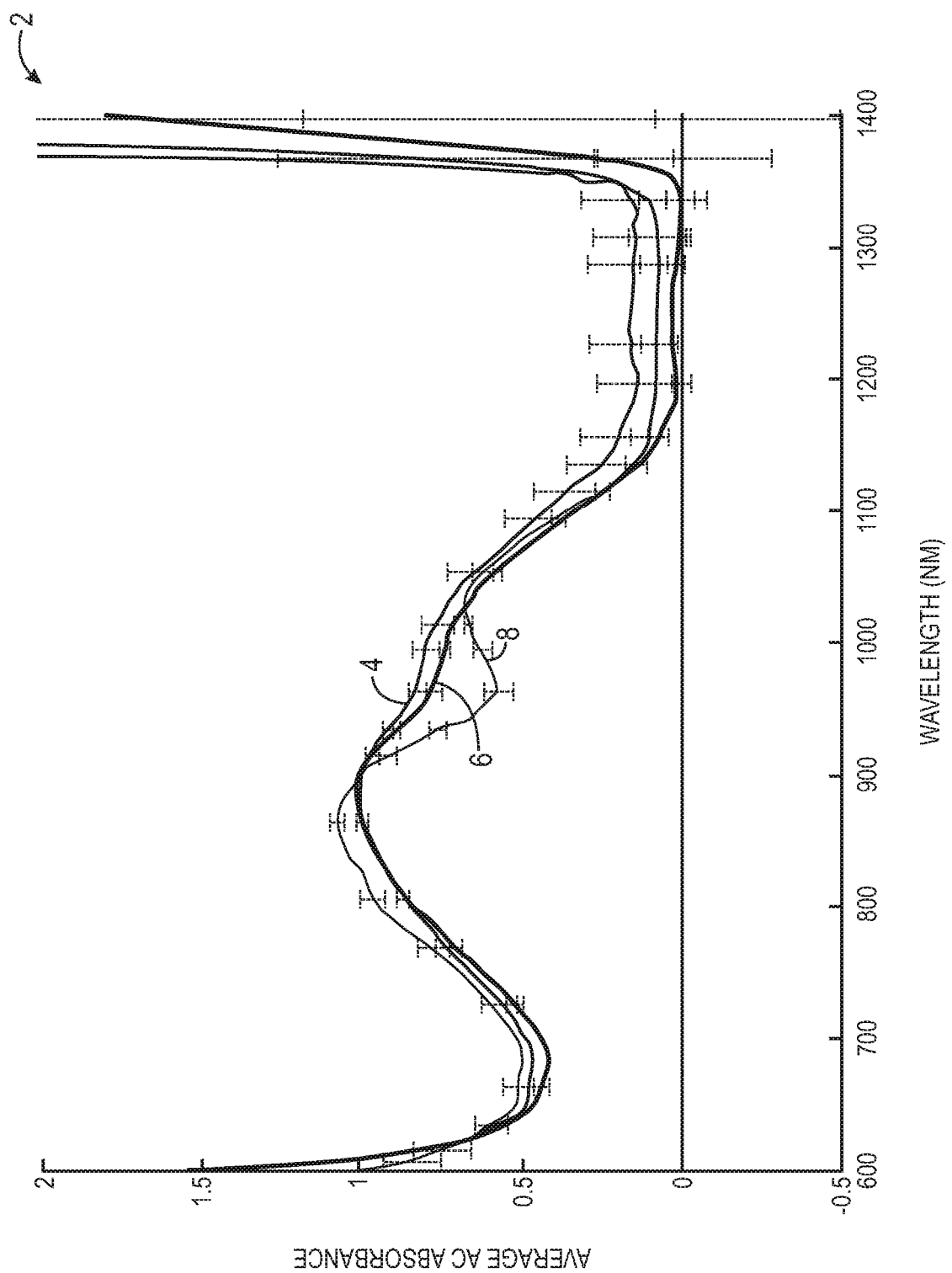
FIG. 1 is a plot of pulse spectra amplitude at varying levels of applied pressure.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments may apply to a variety of photoplethysmographic diagnostic measurements based on pulse spectra detected from patient tissue. For example, pulse oximetry and non-invasive measurements of total hemoglobin may be determined from measurements of pulse spectra on a patient tissue at varying wavelengths of light. Pulse oximetry may involve measurements at wavelengths of approximately 660 nm and 900 nm, and non-invasive measurements of total hemoglobin may involve measurements of wavelengths of approximately 1320 nm and 800-900 nm. As disclosed herein, photoplethysmographic amplitudes were found to vary significantly at certain wavelengths of pulse spectra depending on the amount of pressure with which the sensor is applied to patient tissue. Thus, the present disclosure describes various embodiments of systems, methods, and devices for improving the reliability and reproducibility of measurements taken with photoplethysmographic sensors. Such diagnostic measurements may include pulse oximetry measurements or non-invasive measurements of total hemoglobin.

In experiments carried out to measure pulse spectra on five human subjects, plethysmographic amplitudes were found to vary significantly by pressure. The experiments were carried out using a fiber optic reflectance sensor having a 5 mm diameter ring of illumination fibers surrounded by a bundle of detection fibers. The illumination fibers were illuminated by a 90 W quartz-halogen bulb, and the detection fibers were routed to two different spectrometers to enable the pulse spectra to be measured across the visible and near infer red regions. The first spectrometer (the "Si spectrometer") included an f/8 monochromator (Acton, Model 275) with a grating of 150 grooves/mm blazed at 500 nm and a linear 512 element silicon array (Hamamatsu C5964-0900). The second spectrometer (the "InGaAs spectrometer") included an f/2.8 monochromator (American Holographics, Model 492.85) and a 256-element InGaAs linear array (Sensors Unlimited, Model SU256LX-1.7). Long pass filters with cutoff wavelengths of 475 nm and 900 nm were placed at the entrance ports of the Si and InGaAs spectrometers, respectively, to reduce effects due to higher order grating diffraction. The spectral resolutions of the Si and InGaAs Spectrometers were 10 nm and 18 nm, respectively, and the time resolutions of the spectra acquired by the Si and InGaAs Spectrometers were 84 ms and 23 ms, respectively.

Pulse spectra for five healthy, human subjects who were breathing room air were measured at varying levels of pressure. Raw tissue spectra observed on the patients were converted to absorbance spectra by subtracting the spectrum measured with the light source turned off and dividing by the spectrum measured on a solid reflectance standard (Teflon), and subsequently computing the negative logarithm (base 10) of the result. The absorbance spectra were decimated by wavelength, such that the spacing between channels corresponded to approximately one half of the spectral resolution. The absorbance spectra were then temporally bandpass filtered with lower and upper frequency cutoffs of 0.6 and 4.0 Hz, respectively. Additionally, the absorbance spectra were Fourier phase filtered using wavelengths of 500 nm and 1000 nm, respectively, as reference signals for the pulse spectra detected at the Si and InGaAs Spectrometers. Pulse spectra were constructed by computing the slope of a least-squares linear fit to the absorbance at each wavelength versus a reference wavelength.

Measurements of the pulse spectra were collected on the middle or ring finger of five volunteer subjects at three different pressures: "low," "medium," and "high." "Low" pressure was a pressure only just sufficient to contact the finger with the sensor, occurring at approximately 5 mm Hg. "High" pressure was a pressure just below the pressure required to fully extinguish the photoplethysmographic waveform at a certain reference wavelength, such as 900 nm, occurring at approximately 125 mm Hg. "Medium" pressure was a pressure of approximately one-half of the "high" pressure, occurring at approximately 60 mm Hg. Three replicate measurements were performed at each pressure, with pressures being measured using a piezo-resistive sensor (Flexiforce B201, Tekscan) shaped to surround the illumination fiber ring. Table 1 below summarizes the average and standard deviation of the pressures applied to the tissues of the patient, which varied from patient to patient.

TABLE 1

Pressures applied to the tissue at the sensor site (mm Hg)

| Pressure | Average | Between subj. stand. dev. |
|---|---|---|
| High | 126 | 21 |
| Medium | 60 | 9 |
| Low | 5 | 4 |

As noted above, pulse spectra may be employed for use in various photoplethysmographic diagnostic measurements, such as pulse oximetry and non-invasive total measurement of hemoglobin. In the case of pulse oximetry, the pulse spectrum may be measured at approximately 660 nm and at approximately 900 nm. As such, pulse oximetry may benefit from a consistent relationship between the measured amplitudes at approximately 660 nm and at approximately 900 nm. The pulse spectra experimentally collected from the five human subjects were compared at wavelengths of 660 nm and 900 nm, the results of which are shown below in Table 2.

TABLE 2

Pulse amplitude measured at 660 nm (normalized to 900 nm) as a function of pressure

| Pressure | Mean amplitude | Within subj. std. dev. | Between subj. std. dev. |
|---|---|---|---|
| Low | 0.478 | 0.030 | 0.069 |
| Medium | 0.444 | 0.022 | 0.042 |
| High | 0.514 | 0.039 | 0.048 |

Table 2 relates the amplitude of the measured pulse spectra at 660 nm to that of 900 nm. As indicated by Table 2, the mean amplitude at 660 nm may be dependent on the amount of pressure applied to the sensor. In particular, application of "medium" pressure results in the lowest standard deviation of the mean amplitude on a particular human subject, which is noted as "within subj.," as well as across the group of subjects, noted at "between subj." Since all of the subjects were healthy and breathing room air, their arterial oxygen saturation percentages were all expected to be near 100%. Within-subject and between-subject variations were therefore expected to be indicative of the reproducibility of the measurement. In both cases, the "medium" pressure measurement proved to be the most reproducible of those tested. However, a fraction of the "high" pressure other than the "medium" pressure may be determined to produce more reproducible results. For example, with further experimentation, it may be determined that a pressure equivalent to approximately one-quarter of the "high" pressure or three-quarters of the "high" pressure may produce results more reproducible than results produced using the tested "medium" pressure.

For the purpose of measuring total hemoglobin in blood non-invasively, a pulse amplitude at 1320 nm relative to that at 800-900 nm, as well as other possible wavelengths, may be useful. As such, non-invasive measurement of total hemoglobin may also benefit from a consistent relationship between the measured amplitudes at approximately 1320 nm and at approximately 800-900 nm. The pulse spectra experimentally collected from the five human subjects were compared at wavelengths of 1320 nm and 900 nm, the results of which are shown below in Table 3.

TABLE 3

Pulse amplitude measured at 1320 nm (normalized to 900 nm) as a function of pressure

| Pressure | Mean amplitude | Within subj. std. dev. | Between subj. std. dev. |
|---|---|---|---|
| Low | 0.129 | 0.061 | 0.137 |
| Medium | −0.009 | 0.031 | 0.038 |
| High | 0.059 | 0.046 | 0.119 |

Table 3 relates the amplitude of the measured pulse spectra at 1320 nm to that of 900 nm. As shown in Table 3, the experimental data may indicate that the pulse amplitude at 1320 nm is strongly dependent on the pressure applied to the sensor. The data may also indicate that by applying a "medium" pressure, the amplitude at 1320 nm may be reproducible as measured both on a particular subject and across a group of subjects.

FIG. 1 is a plot 2 of average amplitudes obtained for the three pressures "low," "medium," and "high" along a spectrum from 600 nm to 1400 nm. As described above, "low" pressure represents a pressure only just sufficient to contact the finger with the sensor, occurring at approximately 5 mm Hg; "high" pressure represents a pressure just below the pressure required to fully extinguish the photoplethysmographic waveform at a certain reference wavelength, such as 900 nm, occurring at approximately 125 mm Hg; and "medium" pressure represents a pressure of approximately one-half of the "high" pressure, occurring at approximately 60 mm Hg. The ordinate of the plot 2 indicates AC absorbance averaged across all tests as reflected in the photoplethysmographic amplitude (normalized to 900 nm), and the abscissa of the plot 2 indicates wavelength of the spectrum in units of nanometers (nm).

In the plot 2 of FIG. 1, a curve 4 represents averaged AC spectra obtained at the "low" pressure, a curve 6 represents averaged AC spectra obtained at the "medium" pressure, and a curve 8 represents averaged AC spectra obtained at the "high" pressure. Error bars associated with each curve 4, 6, and 8 represent the standard deviation between subjects for pulse spectra obtained at the "low," "medium," and "high" pressures, respectively. As is apparent from the plot, the "medium" pressure curve 6 has the least variability across substantially the entire the range of disclosed wavelengths. Thus, it should be understood that a "medium" pressure applied on a plethysmographic sensor may provide the greatest reproducibility between subjects across wavelengths of interest in plethysmographic diagnostic measurements.

Figure 2:
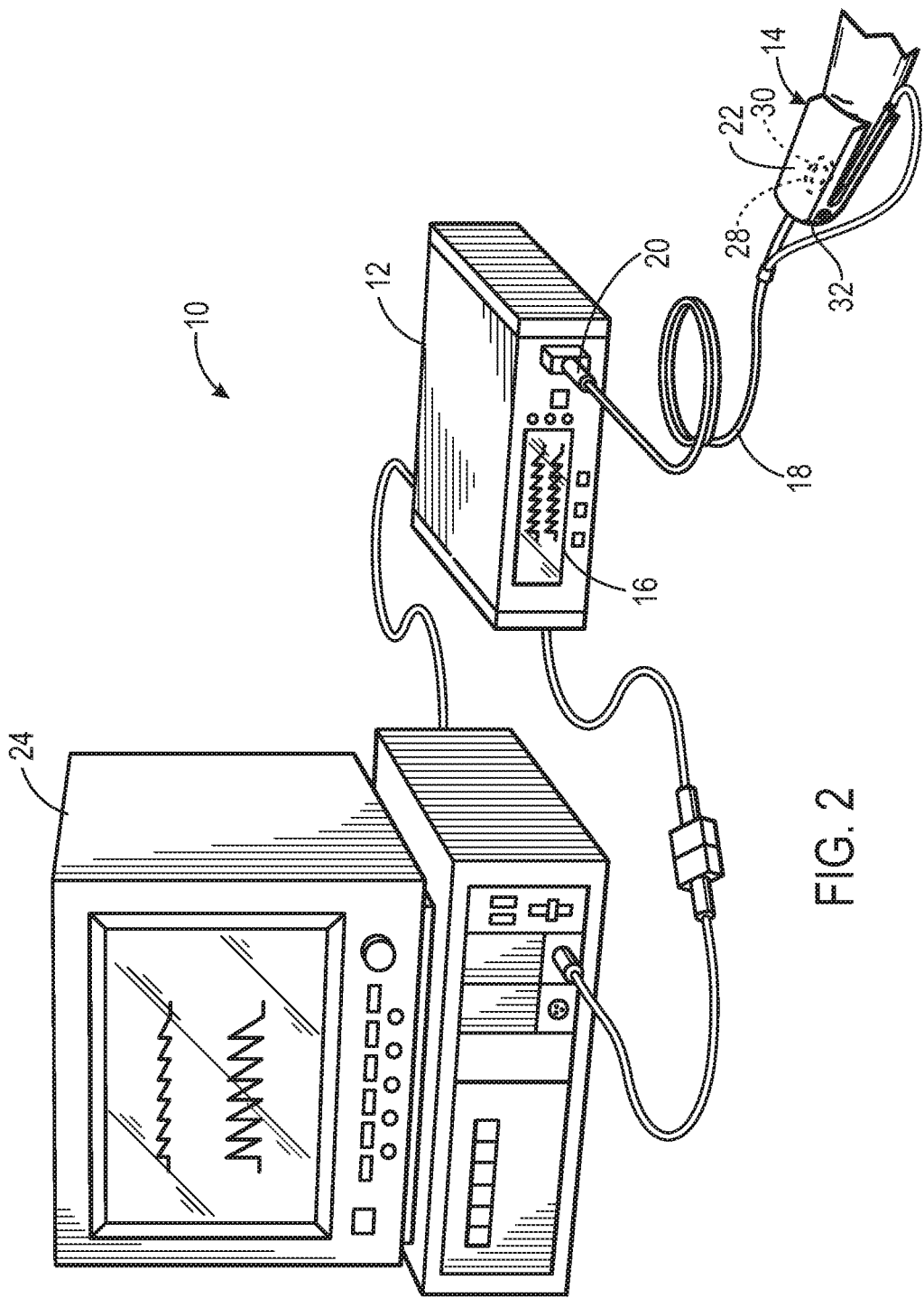
FIG. 2 is a perspective view of a photoplethysmographic system, in accordance with an embodiment.

With the foregoing in mind, FIG. 2 illustrates a perspective view of a photoplethysmography system 10 in accordance with present embodiments for obtaining consistent and reproducible diagnostic measurements. The system 10 may be employed to observe the blood constituents of a patient's arterial blood by emitting light at particular wavelengths into tissue and detecting the light after dispersion and/or reflection by the tissue. For example, diagnostic measurements for pulse oximetry may involve photoplethysmographic measurements at approximately 660 nm and at approximately 900 nm, and diagnostic measurements for non-invasively measuring total hemoglobin may involve photoplethysmographic measurements at approximately 1320 nm and at approximately 800-900 nm.

The system 10 may include a patient monitor 12 that communicatively couples to a photoplethysmographic sensor 14. The patient monitor 12 may include a display 16, a memory, a processor, and various monitoring and control features. The patient monitor 12 may be configured to perform pulse oximetry measurements, calculations, and control algorithms using high precision values in accordance with present embodiments. The photoplethysmographic sensor 14 may include a sensor cable 18, a connector plug 20, and a sensor assembly or body 22 configured to attach to a patient (e.g., a patient's finger, ear, forehead, or toe). In the illustrated embodiment, the sensor assembly is configured to attach to a finger and to apply a pressure sufficient to exclude extraneous extravascular fluid while permitting arterial blood flow in the pulsatile tissue of the finger. The system 10 may include a separate display feature 24 that is communicatively coupled with the patient monitor 12 to facilitate presentation of plethysmographic data and that may display a plethysmogram, pulse oximetry information, non-invasive measurement of total hemoglobin, and/or related data.

The photoplethysmographic sensor 14 may include an emitter 28 and a detector 30. When attached to patient tissue, the emitter 28 may transmit light at different wavelengths into the tissue and the detector 30 may receive the light after it has passed through or is reflected by the tissue. The amount of light that passes through the tissue and other characteristics of light waves may vary in accordance with the changing amount of certain blood constituents in the tissue and the related light absorption and/or scattering. For example, the system 10 may emit light from two or more LEDs or other suitable light sources, such as lasers or incandescent light sources guided by fiber optics, into the pulsatile tissue. The reflected or transmitted light may be detected with the detector 30, such as a photodiode or photo-detector, after the light has passed through or has been reflected by the pulsatile tissue.

The photoplethysmographic sensor 14 may facilitate certain diagnostic measurements by specifically examining responses by the tissue at certain wavelengths. For example, to conduct pulse oximetry measurements, the emitter 28 of the photoplethysmographic sensor 14 may emit light of wavelengths of approximately 660 nm and 900 nm. To conduct non-invasive measurements of total hemoglobin, the emitter 28 of the photoplethysmographic sensor 14 may emit light of wavelengths of approximately 1320 nm and 800-900 nm. Because the ratio of amplitudes for measurements obtained at one wavelength to another wavelength may vary with pressure, a pressure device 32 may apply an optimum amount of pressure between the photoplethysmographic sensor 14 and the patient tissue, enhancing the reproducibility of measurements taken at the various wavelengths. In the embodiment of FIG. 2, the photoplethysmographic sensor 14 may be shaped as a clip and the pressure device 32 may cause the sensor body 22 to fold or compress around the patient's finger. The pressure device 32 may be controlled manually or automatically by the patient monitor 12.

Figure 3:
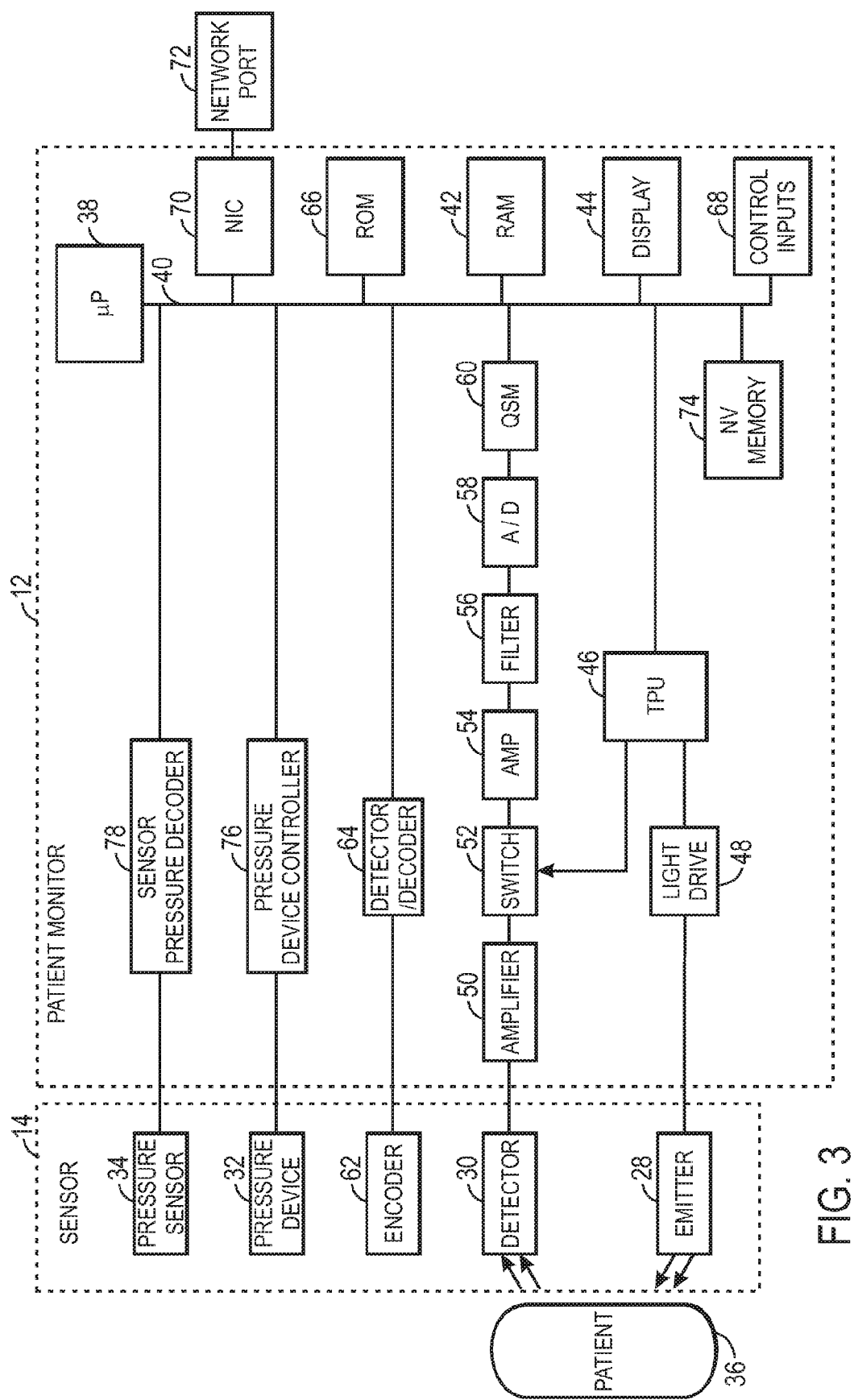
FIG. 3 is a block diagram of a photoplethysmographic system, in accordance with an embodiment.

FIG. 3 is a block diagram of an embodiment of the monitoring system 10 that may be configured to implement the techniques described herein. By way of example, embodiments of the system 10 may be implemented with any suitable patient monitor, such as those available from Nellcor Puritan Bennett LLC. The system 10 may include the patient monitor 12 and the photoplethysmographic sensor 14, which may be configured to obtain a plethysmographic signal from patient tissue at certain predetermined wavelengths at an optimum pressure. The photoplethysmographic sensor 14 may be communicatively connected to the patient monitor 12 via a cable or wireless device. When the system 10 is operating, light from the emitter 28 may pass into a patient 36 and be scattered and detected by the detector 30. The patient monitor 12 may include a microprocessor 38 connected to an internal bus 40. Also connected to the bus 40 may be a RAM memory 42 and a display 44. A time processing unit (TPU) 46 may provide timing control signals to light drive circuitry 48 which may control when the emitter 28 is illuminated, and if multiple light sources are used, the multiplexed timing for the different light sources. The TPU 46 may also control the gating-in of signals from the detector 30 through an amplifier 50 and a switching circuit 52. These signals may be sampled at the proper time, depending upon which of multiple light sources is illuminated, if multiple light sources are used. The received signal from the detector 30 may be passed through an amplifier 54, a low pass filter 56, and an analog-to-digital converter 58. The digital data may then be stored in a queued serial module (QSM) 60, for later downloading to the RAM 42 as the QSM 60 fills up. In one embodiment, there may be multiple parallel paths of separate amplifier, filter and A/D converters for multiple light wavelengths or spectra received.

In an embodiment, the photoplethysmographic sensor 14 may also contain an encoder 62 that provides signals indicative of the wavelength of one or more light sources of the emitter 28 to allow the patient monitor 12 to select appropriate calibration coefficients for calculating a physiological parameter such as blood oxygen saturation. By way of example, present embodiments may be implemented with any suitable photoplethysmographic sensor, such as those available from Nellcor Puritan Bennett LLC. The encoder 62 may, for instance, be a coded resistor, EEPROM or other coding devices (such as a capacitor, inductor, PROM, RFID, a barcode, parallel resonant circuits, or a colorimetric indicator) that may provide a signal to the processor 38 related to the characteristics of the photoplethysmographic sensor 14 that may allow the processor 38 to determine the appropriate calibration characteristics for the photoplethysmographic sensor 14. Further, the encoder 62 may include encryption coding that prevents a disposable part of the photoplethysmographic sensor 14 from being recognized by a processor 38 that is not able to decode the encryption. For example, a detector/decoder 64 may be required to translate information from the encoder 62 before it can be properly handled by the processor 38.

In various embodiments, based at least in part upon the value of the received signals corresponding to the light received by detector 30, the microprocessor 38 may calculate a physiological parameter using various algorithms. These algorithms may utilize coefficients, which may be empirically determined, corresponding to, for example, the wavelengths of light used. These may be stored in a ROM 66. In a two-wavelength system, the particular set of coefficients chosen for any pair of wavelength spectra may be determined by the value indicated by the encoder 62 corresponding to a particular light source in a particular sensor 14. For example, the first wavelength may be a wavelength that is highly sensitive to small quantities of deoxyhemoglobin in blood, and the second wavelength may be a complimentary wavelength. Specifically, for example, such wavelengths may be produced by orange, red, infrared, green, and/or yellow LEDs. Different wavelengths may be selected with control inputs 68. The control inputs 68 may be, for instance, a switch on the monitor, a keyboard, or a port providing instructions from a remote host computer.

The patient monitor 12 may be connected to a network via a network interface 70. The network interface 70 may implement any suitable networking technology or protocol, such as Ethernet, wireless Ethernet, and so forth. The network interface 70 may be connected to a network port 72 via a network cable or via a wireless connection. Additionally, the patient monitor 12 may include a non-volatile memory 74 that may store caregiver preferences, patient information, or any other information useful for configuring the patient monitor 12. The software for performing the configuration of the patient monitor 12 and retrieval of information over the network interface 70 may also be stored on the memory 74, or may be stored on the ROM 66.

The photoplethysmographic sensor 14 may include the pressure device 32 and/or the pressure sensor 34, which may operably connect to the patient monitor 12. Specifically, the pressure device 34 may be controlled by a pressure device controller 76 in the patient monitor 12, which may increase or decrease the pressure of the photoplethysmographic sensor 14 on the patient 36 to achieve a desired pressure. The pressure device controller 76 may transmit an electronic signal or a signal of supplied liquid or gas to control the pressure device 34. Based on routines stored in RAM 42, ROM 66, and/or nonvolatile memory 74 that may be executed by the microprocessor 38, the pressure device controller 76 may increase or decrease pressure until an optimum pressure for a desired diagnostic measurement is obtained. The pressure sensor 34 may provide an indication of the current pressure to a sensor pressure decoder 78 in the patient monitor 12. As the pressure device controller 76 instructs the pressure device 32 to increase or decrease the pressure applied to the patient 36, sensor pressure decoder 78 may provide the microprocessor 38 with data indicating the current applied pressure. Such data may be used, for example, to provide closed-loop feedback to the microprocessor 38. Based on such closed-loop feedback, the microprocessor 38 may suitably control the applied pressure with a PID controller or a PID control algorithm, which may be implemented in software running on the microprocessor 38.

In one embodiment, the pressure device controller 76 may instruct the pressure device 32 to maintain the pressure of the photoplethysmographic sensor 14 against the patient 36 at a low level when plethysmographic diagnostic measurements are not being obtained. When such plethysmographic diagnostic measurements are being obtained, (e.g., just prior to and during measurement of the pulse amplitude of the patient 36), the pressure device controller 76 may instruct the pressure device 32 to increase the pressure against the patient 36 to an optimal value of pressure (e.g., approximately half of a maximal value). In this way, the electronic patient monitor 12 may obtain reproducible results across a range of subjects and time periods, and the effect of the pressure applied by the photoplethysmographic sensor 14 on the blood circulation in the tissue of the patient 36 may be minimized.

Figure 4:
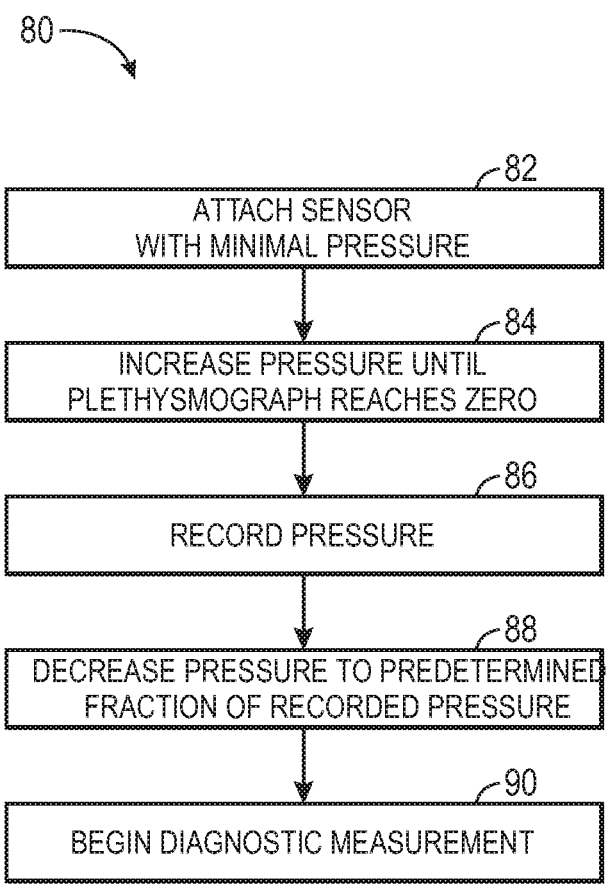
FIG. 4 is a flowchart describing a method of determining and applying a pressure with a photoplethysmographic sensor, in accordance with an embodiment.

FIG. 4 is a flowchart 80 of an embodiment of a method for performing a desired photoplethysmographic diagnostic measurement at an optimum pressure. At the optimum pressure, the photoplethysmographic sensor 14 may provide reproducible photoplethysmographic waveforms across a range of patients and times, which may translate into reproducible diagnostic measurements. Steps of the flowchart 80 may be performed manually by a medical practitioner or automatically by the photoplethysmography system 10, as identified in the discussion below.

The flowchart 80 may begin with a first step 82, when a medical practitioner may attach the photoplethysmographic sensor 14 with minimal pressure to a tissue site, such as a finger, on the patient 36. Such a minimal pressure may be, for example, approximately 1-10 mm Hg. In step 84, the medical practitioner may manually increase the pressure or the patient monitor 12 may control the pressure device 32 to increase the pressure against the patient 36 while observing a photoplethysmographic waveform for a predetermined wavelength of light. The predetermined wavelength of the photoplethysmographic waveform may be chosen based on the type of diagnostic measurement that is intended. For example, if the desired diagnostic measurement includes pulse oximetry, the predetermined wavelength of the photoplethysmographic waveform may be approximately 660 nm or 900 nm. If the desired diagnostic measurement includes non-invasive measurement of total hemoglobin, the predetermined wavelength of the photoplethysmographic waveform may be approximately 1320 nm or 900 nm. As the pressure is increased in the step 86, the earliest point at which the photoplethysmographic waveform reaches a minimum at the predetermined wavelength may represent a maximal sensor pressure. Such a maximal pressure is believed to cause extravascular fluid to exit the tissue site and arterial blood flow to substantially cease when applied against the tissue site of the patient 36, and may be, for example, approximately 100-150 mm Hg.

In step 86, the medical practitioner or the patient monitor 12 may record the maximal pressure using the pressure sensor 34. In step 88, the medical practitioner or the patient monitor 12 may cause the pressure of the photoplethysmographic sensor 14 against the patient 36 to be a predetermined fraction of the maximal pressure recorded in step 86. For example, the pressure may be decreased to approximately half of the maximal pressure, since a "medium" pressure has been experimentally shown to be reproducible across a range of subjects and time periods. At such a medium pressure, it is believed that most extravascular fluid is excluded from the tissue site while most arterial blood continues to flow. It should be appreciated, however, that other predetermined fractions of the maximal pressure recorded in step 86 may be applied in step 88. Such predetermined fractions may be any fraction of the maximal pressure greater than the minimal pressure and less than the maximal pressure, and may be, for example, approximately one-quarter, one-third, two-thirds, or three-quarters of the maximal pressure. For example, if the pressure recorded in step 86 is approximately 100-150 mm Hg, the medium pressure applied in step 88 may be approximately 50-70 mm Hg for patients with normal blood pressure.

In step 90, one or more diagnostic measurements of interest may be taken while the predetermined fraction of the maximal pressure is being applied. For example, while the predetermined fraction of the maximal pressure is being applied, the photoplethysmographic system 10 may take a pulse oximetry reading based on, for example, wavelengths of approximately 660 nm and 900 nm. Additionally or alternatively, the photoplethysmographic system 10 may take measurements of total hemoglobin based on, for example, wavelengths of approximately 1320 nm and 800-900 nm.

Steps 84-88 above may be performed only when the photoplethysmographic sensor 14 is first placed on the patient 36. Alternatively, to further increase measurement reproducibility, steps 84-88 may be repeated each time a diagnostic measurement is to be obtained, and after the measurement has been obtained, the pressure may be reduced to the minimal pressure. In another embodiment, steps 84-86 may be performed at a periodic interval (e.g., once every hour, half hour, 15 minutes, etc.) or after a predetermined number of diagnostic measurements have been obtained, and step 88 may be performed each time a diagnostic measurement is to be obtained.

Figure 5:
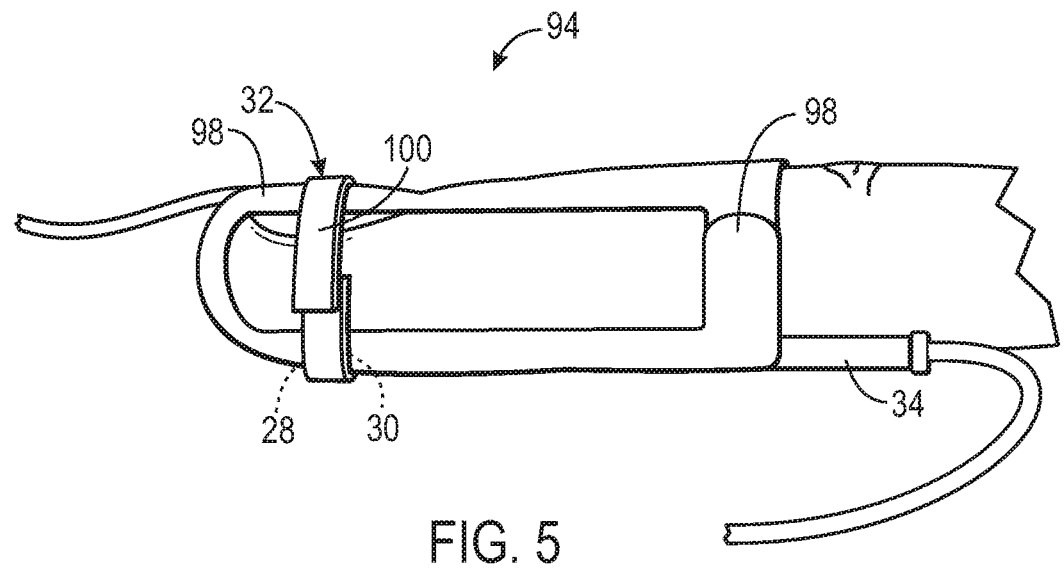
FIG. 5 is a perspective view of a photoplethysmographic sensor having an adhesive for applying pressure against a patient, in accordance with an embodiment.
Figure 6:
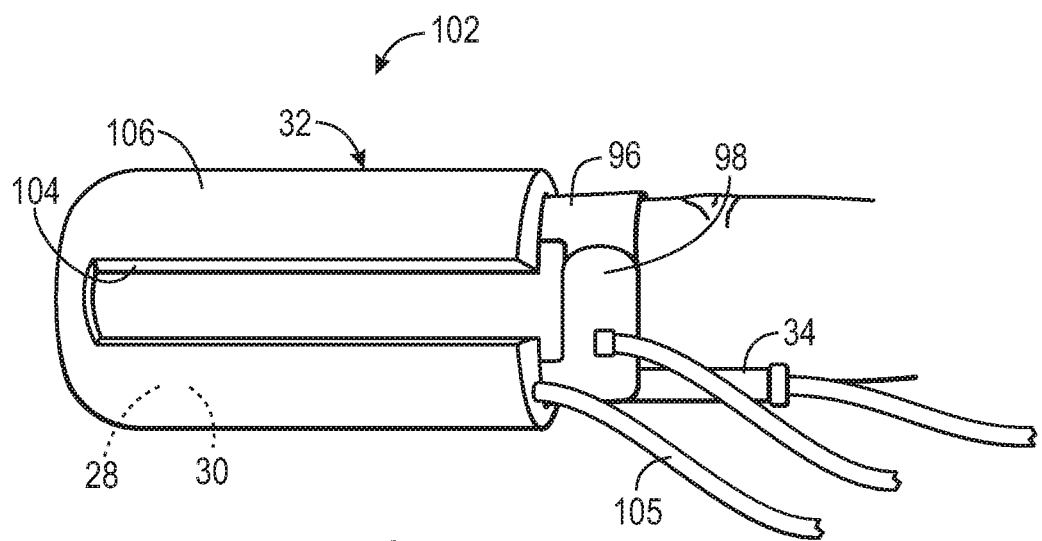
FIG. 6 is a perspective view of a photoplethysmographic sensor having an inflatable balloon or bladder for applying pressure to a patient, in accordance with an embodiment.
Figure 7:
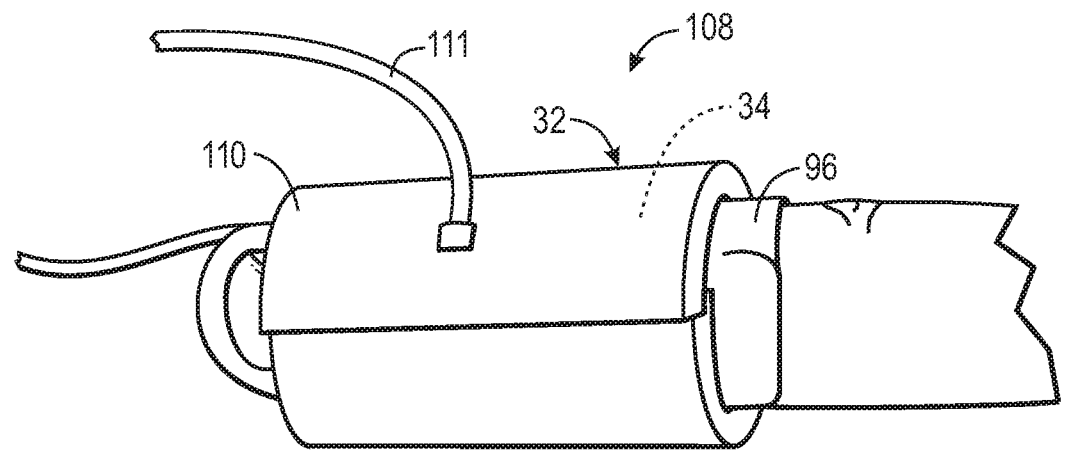
FIG. 7 is a perspective view of a photoplethysmographic sensor having an inflatable cuff for applying pressure on a patient, in accordance with an embodiment.

FIGS. 5-7 represent various alternative embodiments of the photoplethysmographic sensor 14 for practicing the embodiment of the method of the flowchart 80 of FIG. 4. In particular, FIG. 5 illustrates a photoplethysmographic sensor with a manually-controlled wrap-based pressure device 32, FIG. 6 illustrates a photoplethysmographic sensor with an inflatable-balloon-based pressure device 32, and FIG. 7 illustrates a photoplethysmographic sensor with an inflatable-cuff-based pressure device 32. Turning first to FIG. 5, a wrap-based photoplethysmographic sensor 94 may enable a medical practitioner to manually perform the method described in flowchart 80. The sensor 94 may include any underlying photoplethysmographic sensor 96, which may include, for example, an emitter 28 and a detector 30 in either a transmission-type or reflectance-type configuration. The sensor 96 may be formed from a flexible material, such as cloth or soft plastic, and may include adhesive straps 98 to attach the sensor 96 to the patient 36.

A medical practitioner may use a wrap-based pressure device 32, illustrated in FIG. 5 as a foam adhesive 100, to maintain pressure on the sensor 96. Additionally or alternatively, the foam adhesive 100 may be or include any material that may be wrapped around the sensor 96, such as gauze, tape, elastic bands, bands of Velcro-type hook-and-loop fasteners, and so forth. A pressure sensor 34 may be placed beneath or attached to the sensor 96 to monitor the amount of pressure applied. To carry out the steps of the flowchart 80 using the wrap-based photoplethysmographic sensor 94, a medical practitioner may first loosely attach the sensor 96 to the patient 36 by attaching the adhesive straps 98; the pressure sensor 34 should indicate a minimal pressure of approximately 1-10 mm Hg. Next, the medical practitioner may apply pressure on the sensor 96 at the locations of the admitter 28 and detector 30, observing the plethysmographic waveform displayed on the patient monitor 12 at the predetermined wavelength. When the plethysmographic waveform extinguishes to a minimum, the medical practitioner may record the maximal pressure indicated by the pressure sensor 34. The medical practitioner may subsequently attach the foam adhesive 100 tightly enough to achieve a pressure of approximately half of the maximal pressure before taking a diagnostic measurement of interest.

FIG. 6 illustrates a photoplethysmographic sensor 102 with an inflatable-balloon-based pressure device 32, which may represent another embodiment of the photoplethysmographic sensor 14 and which may also enable the method of the flowchart 80. The sensor 102 may include, for example, the flexible sensor 96 having the emitter 28 and detector 30, which may attach to a tissue site of the patient 36 using the adhesive straps 98. As in the sensor 94 of FIG. 5, the pressure sensor 34 beneath the sensor 96 may enable monitoring of the pressure applied to the patient 36. The pressure device 32 of the photoplethysmographic sensor 102 may be include an inflatable balloon or bladder 104 attached to an inflation tube 105 and surrounded by an inflexible casing 106. The inflatable balloon or bladder 104 may be formed from any flexible material capable of holding a gas or liquid supplied via the inflation tube 105, such as latex or flexible plastic. The inflexible casing 106 may include, among other things, rigid plastic or metal to hold the inflatable balloon or bladder 104 against the patient 36 while inflated.

The sensor 102 of FIG. 6 may be used to carry out the method of the flowchart 80 of FIG. 4 in a variety of manners. For example, the inflatable balloon or bladder 104 may be pumped manually by a medical practitioner, who may carry out the method of the flowchart 80 in a manner similar to that described above with reference to FIG. 5. Additionally or alternatively, the patient monitor 12 may automatically control the sensor 102 to carry out the steps 84-90 of the flowchart 80. For example, the pressure device controller 76 of the patient monitor 12 may be configured to inflate the balloon or bladder 104. When a plethysmographic waveform signal from the photoplethysmographic sensor 102 extinguishes to a minimum at a predetermined wavelength, the patient monitor 12 may record the pressure indicated by the pressure sensor 34 and as determined by the sensor pressure decoder 78, storing the pressure value in the RAM 42 or the nonvolatile memory 74. The pressure device controller 76 may next cause the balloon or bladder 104 to deflate to approximately half of the stored pressure value. Having obtained an approximately optimum "medium" pressure, the patient monitor 12 may next obtain a diagnostic measurement of interest, such as a pulse oximetry measurement or a non-invasive measurement of total hemoglobin.

FIG. 7 illustrates a photoplethysmographic sensor 108 with an inflatable-cuff-based pressure device 32, which may represent another embodiment of the photoplethysmographic sensor 14 and which may also enable the method of the flowchart 80. As shown in FIG. 7, the photoplethysmographic sensor 108 may include the flexible sensor 96, over which an inflatable cuff 110 may be placed. Additionally or alternatively, the inflatable cuff 110 may incorporate the elements of the flexible sensor 96, such as the emitter 28 and the detector 30, which may be sewn into the inflatable cuff 110. The inflatable cuff 110 may function in a substantially similarly manner as a blood pressure cuff, by inflating or deflating in response to a supplied liquid or gas from an inflation tube 111. Like the inflatable balloon or bladder 104 shown in FIG. 6, the inflatable cuff 110 may be controlled manually by a medical practitioner or automatically via the patient monitor 12.

Figure 8:
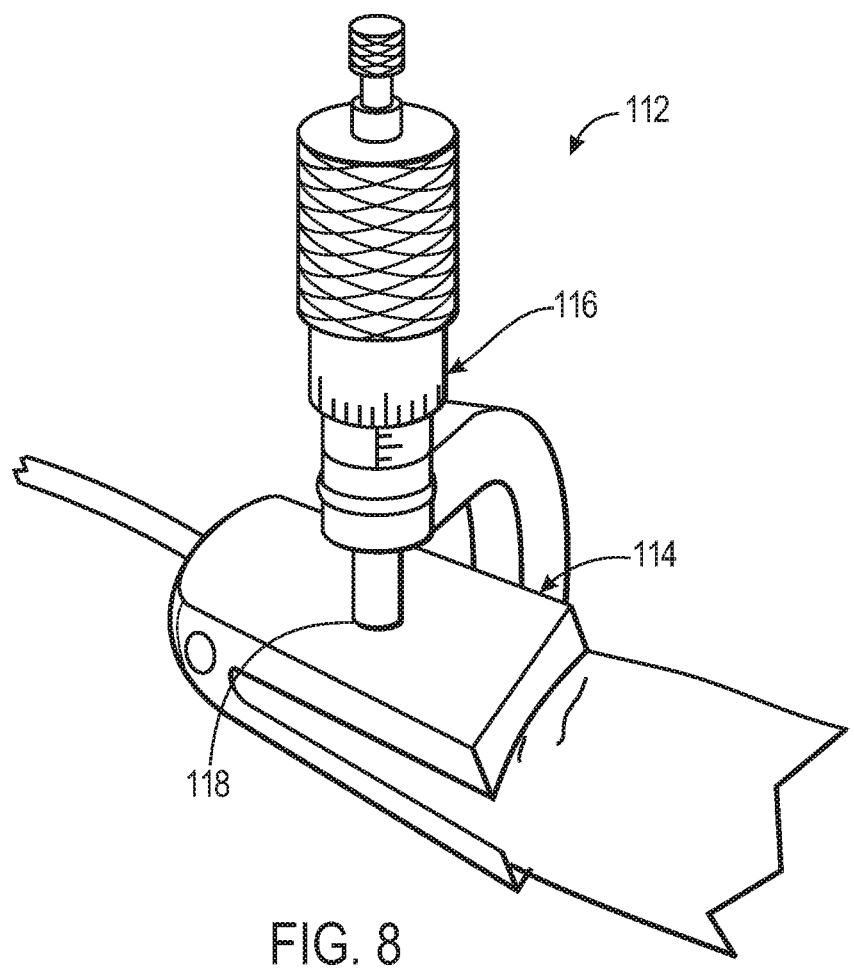
FIG. 8 illustrates a perspective view of a system for obtaining a diagnostic measurement using a photoplethysmographic sensor, in accordance with an embodiment.
Figure 9:
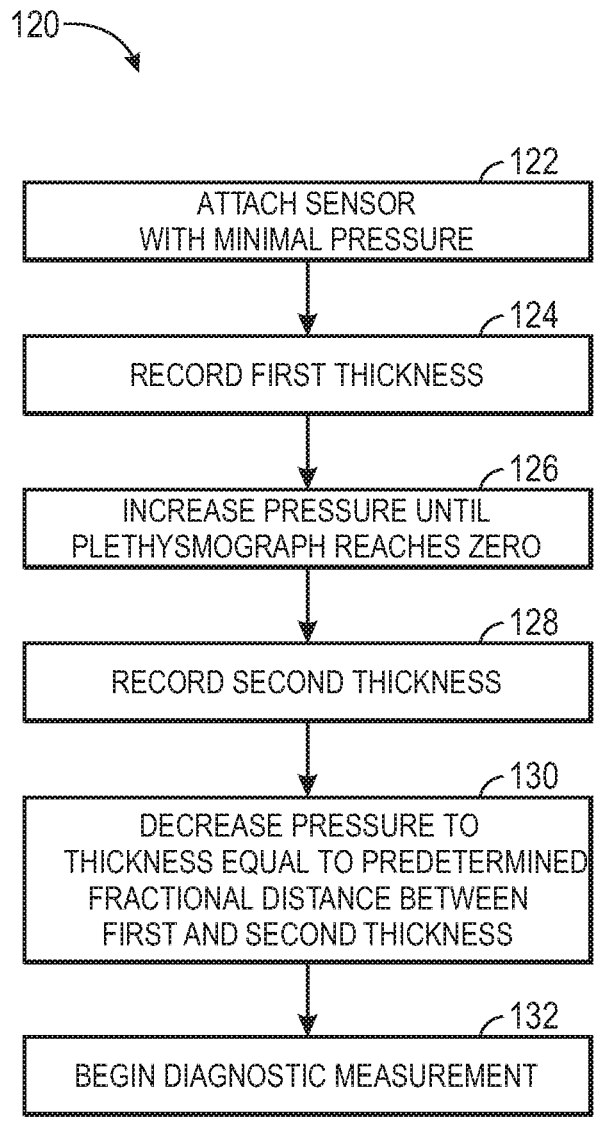
FIG. 9 is a flowchart describing a method of obtaining a diagnostic measurement using the system of FIG. 8, in accordance with an embodiment.

FIGS. 8 and 9 relate to an alternative method of determining an optimal "medium" pressure to achieve reproducible photoplethysmographic data across patients and times. Specifically, FIGS. 8 and 9 describe embodiments that determine an optimum pressure by proxy using measured thicknesses of a photoplethysmographic sensor against patient tissue. As shown in FIG. 8, a thickness-measurement-based photoplethysmographic sensor system 112 may include a photoplethysmographic sensor 114, which may be a finger clip photoplethysmographic sensor similar to the photoplethysmographic sensor 14, and a thickness-measuring device 116, which may be a micrometer. The thickness measuring device 116 may apply pressure at a point 118, representing an approximate location of an emitter 28 and detector 30 in the sensor 114. In some embodiments, the thickness-measuring device 116 may be electronic and controllable by the patient monitor 12 in the same general manner as the pressure control device 32, and may additionally or alternatively provide thickness measurements to the patient monitor 12 in the same general manner as the pressure sensor 34. A medical practitioner or the patient monitor 12 may generally obtain an approximately optimum predetermined fraction of the maximal pressure with the thickness-measurement-based photoplethysmographic sensor system 112 using an embodiment of a method described with reference to FIG. 9.

A flowchart 120, shown in FIG. 9, describes an embodiment of a method for obtaining a reproducible diagnostic measurement using the thickness-measurement-based photoplethysmographic sensor system 112 of FIG. 8. The embodiment of the method of FIG. 9 may be particularly useful when a pressure sensor 34 is not available. The flowchart 120 may begin with a first step 122, when the medical practitioner may attach the photoplethysmographic sensor 114 with minimal pressure. Using the thickness-measuring device 116, the medical practitioner or the patient monitor 12 may ascertain and record a first thickness around the sensor 114. In step 126, the medical practitioner or the patient monitor 12 may increase the pressure of the photoplethysmographic sensor 114 on the patient 36, which may result in a decreased thickness. In step 128, at the point at which a plethysmographic waveform signal from the photoplethysmographic sensor 114 reaches a minimum, the medical practitioner or the patient monitor 12 may record a second thickness of the photoplethysmographic sensor 114 using the thickness-measuring device 116.

In step 130, the medical practitioner or the patient monitor 12 may allow pressure to decrease by setting the thickness to be approximately equal to a predetermined fractional distance between the first thickness and the second thickness. For example, the thickness may be set to be approximately midway between the first recorded thickness and the second recorded thickness. Such a thickness may generally approximate an optimum "medium" pressure against the patient 36. While continuing to apply the pressure provided by the thickness applied in step 130, the medical practitioner or the patient monitor 12 may begin taking a diagnostic measurement of interest in step 132. The diagnostic measurement of interest may include, for example, a pulse oximetry measurement or a non-invasive measurement of total hemoglobin.

Steps 124-128 above may be performed each time that the photoplethysmographic sensor 14 is first placed on the patient 36. Alternatively, to increase measurement reproducibility, steps 124-128 may be repeated each time a diagnostic measurement is to be obtained, and after the measurement has been obtained, the pressure may be reduced to the minimal pressure. In another embodiment, steps 124-126 may be performed at a periodic interval (e.g., once every hour, half hour, 15 minutes, etc.) or after a predetermined number of diagnostic measurements have been obtained, and step 128 may be performed each time a diagnostic measurement is to be obtained.

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

What is claimed is:

1. A patient monitor comprising:
   circuitry configured to:
      receive a plethysmographic signal from a sensor when the sensor is applied to a patient;
      control a pressure device to increase an applied pressure between the sensor and the patient until identifying a maximal pressure that occurs when the sensor outputs the plethysmographic signal of minimal amplitude; and
      decrease the pressure by a predetermined fraction of the maximal pressure to enable a diagnostic measurement using the sensor.

2. The patient monitor of claim 1, wherein the circuitry is configured to determine the diagnostic measurement based on the plethysmographic signal after decreasing the pressure by the predetermined fraction.

3. The patient monitor of claim 2, wherein the diagnostic measurement comprises a pulse oximetry measurement or a measurement of total hemoglobin, or a combination thereof.

4. The patient monitor of claim 1, wherein the patient monitor is connected to a network via a network interface.

5. The patient monitor of claim 4, wherein the patient monitor is wirelessly connected to the network.

6. The patient monitor of claim 1, wherein the predetermined fraction is approximately one half.

7. The patient monitor of claim 1, wherein the circuitry is configured to control the pressure device to decrease the pressure to between approximately 50 and 70 mm Hg when the maximal pressure is between approximately 100 and 150 mm Hg when the patient has a blood pressure in a normal range.

8. The patient monitor of claim 1, wherein the circuitry is configured to increase or to decrease the pressure applied by the pressure device via an electronic signal.

9. The patient monitor of claim 1, wherein the circuitry is configured to increase or to decrease the pressure applied by the pressure device via a signal of supplied liquid or gas.

10. The patient monitor of claim 1, comprising a pressure sensor decoder configured to receive an indication of the applied pressure via a pressure sensor and to provide the circuitry with data related to the applied pressure.

11. The patient monitor of claim 1, wherein the circuitry is configured to access routines stored in a memory of the patient monitor and to execute the routines to control the pressure device.

12. A system comprising:
a sensor configured to generate a plethysmographic signal when applied to a tissue site of a patient; and
a patient monitor configured to receive the plethysmographic signal and to control a pressure applied to the tissue site, wherein the patient monitor is configured to increase the pressure applied until identifying a maximal pressure that occurs when the plethysmographic signal reaches a minimal amplitude, and to decrease the pressure applied by a predetermined fraction of the maximal pressure to enable a diagnostic measurement using the sensor.

13. The system of claim 12, comprising a pressure device coupled to the sensor, wherein the patient monitor is configured to control the pressure device to increase or to decrease the pressure applied to the tissue site.

14. The system of claim 13, wherein the pressure device comprises a clip, a wrap, an inflatable balloon or bladder, or an inflatable cuff, or any combination thereof.

15. The system of claim 12, comprising a pressure sensor configured to provide data related to the applied pressure to the patient monitor.

16. The system or claim 15, wherein the pressure sensor is coupled to the sensor.

17. The system of claim 12, wherein the patient monitor is configured to determine a pulse oximetry measurement or a measurement of total hemoglobin, or a combination thereof, based on the plethysmographic signal.

18. A patient monitor comprising:
circuitry configured to:
receive a plethysmographic signal from a plethysmographic sensor when the plethysmographic sensor is applied to a patient tissue site;
receive data indicative of a first thickness of a plethysmographic sensor while attached around a patient tissue site at a minimal pressure sufficient to establish contact between the patient and the sensor;
compress the plethysmographic sensor attached around the patient tissue site until a maximal pressure is reached, wherein the maximal pressure is a lowest pressure that causes the plethysmographic sensor to output the plethysmographic signal of minimal amplitude;
receive data indicative of a second thickness of the plethysmographic sensor while attached around the patient tissue site at the maximal pressure; and
decompress the plethysmographic sensor attached around the patient tissue site until the plethysmographic sensor has an intermediate thickness between the first thickness and the second thickness, wherein the intermediate thickness is a predetermined fractional distance between the first and the second thickness.

19. The patient monitor of claim 18, wherein the circuitry is configured to determine a diagnostic measurement of interest using the plethysmographic sensor after the plethysmographic sensor is decompressed to the intermediate thickness.

20. The patient monitor of claim 19, wherein the diagnostic measurement of interest is a pulse oximetry measurement or a measurement of total hemoglobin, or a combination thereof.

* * * * *